United States Patent
Weese et al.

(10) Patent No.: US 11,593,691 B2
(45) Date of Patent: Feb. 28, 2023

(54) INFORMATION RETRIEVAL APPARATUS

(71) Applicant: KONINKLIJKE PHILIPS N.V., Eindhoven (NL)

(72) Inventors: Rolf Jurgen Weese, Norderstedt (DE); Alexandra Groth, Hamburg (DE); Tilman Wekel, Krummesse (DE); Vincent Maurice Andre Auvray, Meudon (FR); Raoul Florent, Ville d'Avray (FR); Romane Isabelle Marie-Bernard Gauriau, Paris (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1096 days.

(21) Appl. No.: 16/313,035

(22) PCT Filed: Jun. 30, 2017

(86) PCT No.: PCT/EP2017/066338
§ 371 (c)(1),
(2) Date: Dec. 23, 2018

(87) PCT Pub. No.: WO2018/002333
PCT Pub. Date: Jan. 4, 2018

(65) Prior Publication Data
US 2019/0164075 A1 May 30, 2019

(30) Foreign Application Priority Data
Jun. 30, 2016 (EP) .................................. 16305806

(51) Int. Cl.
*G09G 5/00* (2006.01)
*G06N 7/00* (2023.01)
(Continued)

(52) U.S. Cl.
CPC ............. *G06N 7/005* (2013.01); *G06F 16/26* (2019.01); *G06F 16/367* (2019.01);
(Continued)

(58) Field of Classification Search
CPC ................. G09G 5/14; G09G 2340/10; G09G 2340/125; G06T 11/60; G06T 15/503
(Continued)

(56) References Cited

U.S. PATENT DOCUMENTS 6,526,415 B2  2/2003  Smith et al.
6,765,574 B1 *  7/2004  Mao ...................... G06T 17/005
345/428

(Continued)

FOREIGN PATENT DOCUMENTS

CN  102609402 B  2/2014
WO  2011071363 A2  6/2011
WO  2014019050 A1  2/2014

OTHER PUBLICATIONS

Banerjee, I., Semantic annotation of 3D anatomical models to support diagnosis and follow-up analysis of musculoskeletal pathologies. International Journal of Comp. Assisted Radiology and Surgery, Nov. 2015], [Retrieved on Apr. 1, 2022]. Retrieved from the Internet: <URL: https://www.researchgate.net/publi (Year: 2015).*
(Continued)

*Primary Examiner* — Gordon G Liu

(57) ABSTRACT

An information retrieval system (IPS). The system comprises an input interface (IN) for receiving a query related to an object of interest. A concept mapper (CM) is configured to map the query to one or more associated concept entries of a hierarchic graph data structure (ONTO). The entries in said structure encode linguistic descriptors of components of a model (GM) for said object (OB). A metric-mapper (MM) is configured to map the query to one or more metric
(Continued)

relationship descriptors. A geo-mapper (GEO) is configured to map said concept entries against the geometric model linked to the hierarchic graph data structure to obtain spatio-numerical data associated with said linguistic descriptors. A metric component (MTC) is configured to compute one or more metric or spatial relationships between said object components based on the spatio-numerical data and the one or more metric relationship descriptors.

20 Claims, 5 Drawing Sheets

(51) Int. Cl.
| | |
|---|---|
| *G06F 16/904* | (2019.01) |
| *G06F 16/901* | (2019.01) |
| *G06F 16/907* | (2019.01) |
| *G06F 16/26* | (2019.01) |
| *G06F 16/36* | (2019.01) |
| *G16H 70/60* | (2018.01) |
| *G16H 50/50* | (2018.01) |
| *G06T 15/00* | (2011.01) |
| *G06T 17/20* | (2006.01) |
| *G16H 50/20* | (2018.01) |
| *G16H 40/63* | (2018.01) |

(52) U.S. Cl.
CPC .......... *G06F 16/904* (2019.01); *G06F 16/907* (2019.01); *G06F 16/9024* (2019.01); *G06T 15/005* (2013.01); *G06T 17/20* (2013.01); *G16H 50/50* (2018.01); *G16H 70/60* (2018.01); *G16H 40/63* (2018.01); *G16H 50/20* (2018.01)

(58) Field of Classification Search
USPC ........................................................ 345/629
See application file for complete search history.

(56) References Cited

U.S. PATENT DOCUMENTS

| | | | |
|---|---|---|---|
| 2006/0020444 A1* | 1/2006 | Cousineau | ............ G06F 40/295 704/1 |
| 2010/0041992 A1 | 2/2010 | Ohuchi et al. | |
| 2011/0087624 A1 | 4/2011 | Hale et al. | |
| 2012/0166462 A1 | 6/2012 | Pathak et al. | |
| 2012/0290976 A1 | 11/2012 | Lahm et al. | |
| 2013/0011027 A1 | 1/2013 | Zillner | |
| 2014/0254906 A1 | 9/2014 | Poole et al. | |

OTHER PUBLICATIONS

Banerjee, et al., Semantic annotation of 3D anatomical models to support diagnosis and follow-up analysis of muscoloskeletal pathologies, International Journal of Computer Assisted Radiology and Surgery, vol. 11, No. 5, Nov. 28, 2015, pp. 707-720.

Palombi, et al., "My Corporis Fabrica: A Unified Ontological, Geometrical and Mechanical View of Human Anatomy", Nov. 29, 2009, Modelling the Physiological Human Workshop, Zermatt, Switzerland, Nov. 29-Dec. 2, 2009 Proceedings, pp. 209-219. (Abstract).

Snomed CT, U.S. National Library of Medicine, http://www.nlm.nih.gov/research/umls/Snomed/snomed_main.html (Abstract).

Ecabert, et al., "Automatic Model-Based Segmentation of the Heart in CT Images", IEEE Trans. Med. Imaging 27(9), 2008, pp. 1189-1201. (Abstract).

Voxel-Man, http://voxel-man.com/, Virtual Reality Medical Training (Abstract).

Biodigital: 3D Human Visualization Platform for Anatomy and Disease, https://www.biodigital.com/, 4 pages (Abstract).

Palombi, "My Corporis Fabrica: an ontology based tool for reasoning and querying on complex anatomical models", Journal of Biomedical Semantics 2014,5:20, pp. 1-13.

Mechouche, et al., "Ontology-Based Annotation of Brain MRI Images", AMIA 2008 Symposium Proceedings, pp. 460-464.

* cited by examiner

INFORMATION RETRIEVAL APPARATUS

This application is the U.S. National Phase application under 35 U.S.C. § 371 of International Application No. PCT/EP2017/066338, filed on Jun. 30, 2017, which claims the benefit of European Application Serial No. 16305806.8, filed Jun. 30, 2016. These applications are hereby incorporated by reference herein.

FIELD OF THE INVENTION

The invention relates to an information retrieval system, to an information retrieval method, to a computer program element and to a computer readable medium.

BACKGROUND OF THE INVENTION

An ontology is a formal linguistic specification of how to represent relationships among objects, concepts, and other entities belonging to a particular area of human experience or knowledge. In the medical field this refers in particular to the relation of anatomical structures, diseases, medical procedures and findings.

An example for such an ontology is the Foundational Model of Anatomy (FMA). Meanwhile FMA was incorporated into a larger ontology which is called "The Systematized Nomenclature of Medicine" (SNOMED) making it more detailed and complete. See for instance, Olivier Bodenreider et al in "Comparing the Representation of Anatomy in the FMA and SNOMED CT", AMIA Symp, Proc, vol 2006, pp 46-50, 2006.

The type of relations defined in this ontology is limited to "is part of" and "is a" relations. However, this type of relation might be of limited value when searching in an ontology with a specific medical question (e.g. in radiation therapy: which are risk structures in the vicinity).

In order to establish a set of principles for ontology development with the goal of creating a suite of orthogonal interoperable reference ontologies in the biomedical domain a team of researchers and developers works on OBO Ontologies. See for instance, Barry Smith et al in "The OBO Foundry: coordinated evolution of ontologies to support biomedical data integration", Nat. Biotechnol., November vol 25(11), pp 1251, 2007. This type of ontology (for instance SNOMED) comprises a larger set of relations.

Banerjee et al., "Semantic annotation of 3D anatomical models to support diagnosis and follow-up analysis of musculoskeletal pathologies", International Journal of Computer Assisted Radiology and Surgery, vo. 11, no. 5, p. 707-720, 2015, suggests the use of an extended ontology also comprising a set of predetermined quantitative attributes.

Correspondinlgy, Palombi et al., "My Corporis Fabrica: A Unified Ontological, Geometrical and Mechanical View of Human Anatomy", 3DPH, Proceedings of Modelling the Physiological Human: 3D Physiological Human Workshop, p. 209-219, 2009, describes an anatomical databased that shall provide a unified ontological, geometrical and mechanical view of human anatomy.

However, extraction of spatial information in relation to the concepts encoded in the ontology is still limited.

SUMMARY OF THE INVENTION

There may therefore be a need to address at least the shortcoming described above. In particular, it would be advantageous to provide a system and method that enable evaluation of spatial or metric queries to derive new spatial or metric relations that may not as such be yet (prior to query) encoded in the ontology.

The object of the present invention is solved by the subject matter of the independent claims where further embodiments are incorporated in the dependent claims. It should be noted that the following described aspect of the invention equally applies to the information retrieval method, to the computer program element and to the computer readable medium.

According to a first aspect of the invention there is provided an information retrieval system. The system comprises an input interface for receiving a query related to an object of interest (such an anatomy or part thereof). A concept mapper is configured to map the query to one or more associated concept entries of a hierarchic graph data structure. The entries in said structure encode linguistic descriptors of components (such a mesh elements) of a model (such as a mesh model) for said object. A metric-mapper is configured to map the query to one or more metric relationship descriptors that describe a metric or spatial relation. A geo-mapper is configured to map said concept entries against the geometric model linked to the hierarchic graph data structure to obtain spatio-numerical data associated with said linguistic descriptors. The spatio-numerical data include in particular coordinates of the respective model components associated with said linguistic descriptors. A metric component is configured to compute one or more metric or spatial relationships between said object components based on the spatio-numerical data and the one or more metric relationship descriptors.

The proposed system allows enhanced spatial information query processing based in particular on an ontology (as one type hierarchical graph structure envisaged herein). Spatial relations are no longer expressed (solely) as "static" entries in the ontology as previously done but the spatial relations are expressed as algorithms that evaluate the ontology together with the (preferably 3D) geometrical model linked into the ontology. By linking an ontology entry (in particular the linguistic descriptor representation) describing an anatomical object/structure to a geometrical 3D model (spatial representation) of the anatomical object/structure, a new type of spatial relation can be introduced (like "on the surface of"). Specifically, these metric or spatial relations are expressed as algorithms that evaluate the combination of linguistic and spatial representation. The new spatial or metric relation can, therefore, be added like any other algorithm to an "algorithmic toolbox" since the spatial relations are not static/hardcoded in the ontology. The spatial or metric relation is novel in the sense that was not encoded in the ontology prior to processing the query.

Preferably, the linking of the geometrical 3D model into the ontology is not fixed. The geometrical model is still a separate entity that can easily be exchanged. Specifically, if for a patient, a patient-specific geometrical 3D model exists, it can replace for instance an average geometrical 3D model that is currently linked to the ontology.

In one embodiment, the information retrieval system comprises a selection component configured to select from the components those satisfying the one or more metric relationships.

In one embodiment, the system comprises a visualizer, configured to render, based on the model, a visualization of the geometrical model or a related model on a displaying device, said visualization including a representation of the selected components.

In one embodiment, the system comprises an output port for outputting a representation of the linguistic descriptors of the selected components. For instance, the descriptors (with our without the components) can be displayed as a list on the display device or are otherwise processed, stored, etc.

In one embodiment, the system comprises a depth-level controller configured to restrict the mapping operation of the concept mapper to concept entries at or up to a pre-defined depth level in the hierarchic graph data structure. This allows saving CPU time and to prevent information overflow.

In one embodiment, the geometric model is a probabilistic geometric model.

In one embodiment the object is an anatomy of a human or animal patient. The model is a generic one or is specific to a patient. In the latter case, the model can be derived from a model-based segmentation of an image of the patient.

In one embodiment, the system comprises an integrator component configured to integrate i) the computed relationships or ii) the one or more metric relationship descriptors into the hierarchic graph data structure.

According to another aspect there is provided an information retrieval method comprises:

receiving a query related to an object of interest;

mapping the query to one or more associated concept entries of a hierarchic graph data structure, the entries in said structure encoding linguistic descriptors of components of a model for said object;

mapping the query to one or more metric relationship descriptors;

mapping said concept entries against a geometric model linked to the hierarchic graph data structure to obtain spatio-numerical data associated with said linguistic descriptors; and computing one or more metric relationships between said object components based on the spatio-numerical data and the one or more metric relationship descriptors. The computation involves in particular finding those components or linguistic descriptors that satisfy the one or more metric relationships.

In one embodiment, the method comprises selecting from the components or linguistic descriptors those satisfying the one or more metric relationships.

In one embodiment, the method comprises rendering, based on the model, a visualization of the prototype on a displaying device, said visualization including a representation of the selected components.

In one embodiment, the method comprises restricting the mapping operation of (in particular) the concept mapper to concept entries at or up to a pre-defined depth level in the hierarchic graph data structure.

In one embodiment, the hierarchic graph data structure includes an ontology.

According to another aspect there is provided a computer program element, which, when being executed by a processing unit is adapted to perform the method.

According to another aspect there is provided a computer readable medium having stored thereon the program element.

Definition

"linguistic descriptors" as used herein is to be construed broadly to include any strings of in particular alpha-numeric character combinations, acronyms. The term is explicitly not restricted to natural language expressions.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
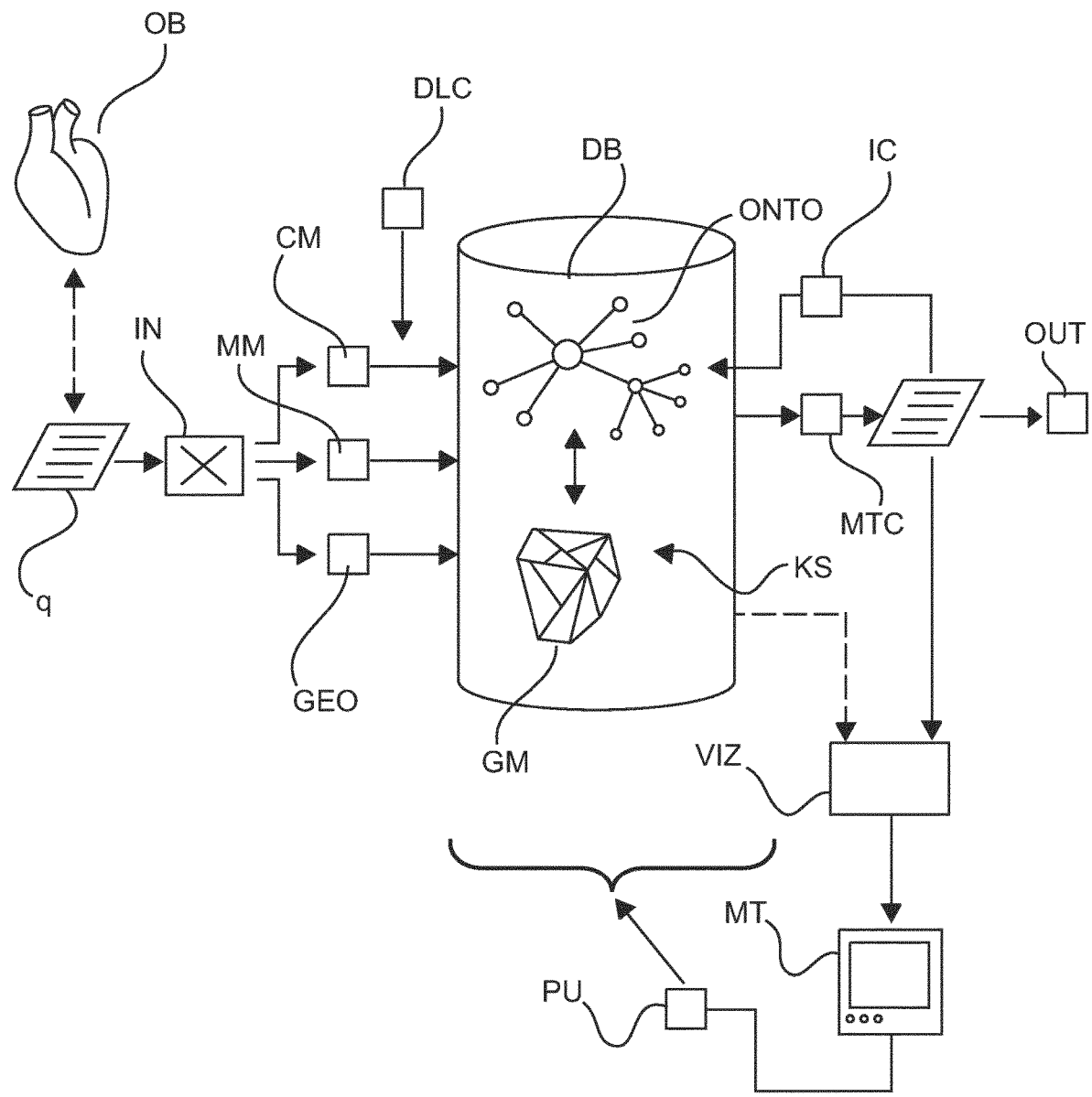
FIG. 1 shows a block diagram of components of an information retrieval system.

With reference to FIG. 1 there is shown a block diagram of components of a computer based information retrieval system or machine mainly envisaged for the medical field, however, other fields of application are not excluded herein.

Specifically, the system is mainly envisaged for processing queries q that include a request (explicit or implicit) formulated in terms of spatial, in particular metric, relation(s). A "spatial" or "geometric" query relates to the topology of an object of interest OB (or part thereof) whilst a "metric" query asks in addition for the topology to be quantified by at least one parameter such as length (cm, mm, inch, foot etc), area ($cm^2$, $mm^2$, etc) or volume ($mm^3$, $cm^{3'}$ milli-liters, liters, etc) quantity (in any units).

Examples for the types of query envisaged for processing include (a) "is structure X on the surface of structure Y?" or (b) "is X located above/behind/left/right/in front of Y" or (c) "is structure X in the neighborhood of D cm of structure Y?", etc. These queries are mere examples, not limiting and the list is non-exhaustive. The variables X, Y used in the above query examples denote names for anatomies or anatomic parts provided by the user in the query, whilst D is a concrete numerical value for a length, area or volume unit expressed numerically (eg, "5 cm") or in natural language (eg "five centimeters") or otherwise as used in the query.

Queries (a),(b) above are examples for topological queries, that is, those that ask only for relative spatial/geometrical relations without (explicit) numerical parameter. In contrast, query (c) is an example for a metric query that does use a (metric) parameter (eg, length D). Mixed types of queries (with topological and metric parts) are also envisaged herein.

In other words, topological queries are "qualitative" queries whilst the metric queries are "quantitative" queries. The proposed system is configured to support either one or, preferably, both types of queries.

The knowledge against which the queries are run is encoded in a combo knowledge structure stored in a memory system, such as a database GM or other. The combo-knowledge structure comprises in digital form a hierarchic graph structure ONTO, such as an ontology. The ontology is coupled or linked to a 2D, preferably 3D, geometric model GM of an object OB of interest. The model may be held in digital form in the same memory or in a different memory. A mere logical linking across a network between the ontology ONTO and the model GM is sufficient for present purposes and it is not required herein the two components to reside in the same memory DB.

The system enables evaluation of spatial or metric queries to derive new spatial or metric relations that may not as such be yet (prior to query) encoded in the ontology ONTO. The geometric model GM relates to a prototype of the object OB. For instance, the model is one of the whole or a part of the human or animal anatomy. The model GM may be a generic one or a patient specific one.

Broadly, the system is configured to exploit the 3D geometric model in combination with the linked ontology ONTO to define geometric relationships or metrical relationships and, optionally, other functionalities derivable from these geometric/metrical relationships. More specifically, the system is configured to evaluate, based in on a query, a combination of linguistic concepts as encoded in the ontology of the combo structure in conjunction with spatial representations as per the 3D geometric model to derive a new spatial relation in respect of the linguistic concepts. The new spatial relationship so derived or computed may then be added into the ontology to so enrich same with previous knowledge which, as such, may not have been present in the ontology before processing of the query.

The system's output comprises an answer to the metric query. The system is configured to provide a quantitative answer rather than a qualitative one, although the combination is also envisaged. The answer is output either numerically as a list data structure including numerical that indicates the answer(s) to the metrical/geometrical question(s) in the one or more query q. In addition to outputting the numerical data, this may be visualized geometrically by a visualizer. The visualizer may be suitably mapping the numerical answer data into a graphical representation or rendering of the model GM. For instance, the numerical in data is displayed on a display device MT in association with the ontology concepts such as the anatomic parts, diseased anatomical area, etc., that were referred to in the query. The visualizer output and the manner or rendering may be fixed by the program designer or, preferably, these are user adjustable.

The visualization operation may further include effecting displaying further concepts associated with the anatomic parts, such as findings, measurements or related actions (possible treatment or diagnostic steps), earlier reports/prescriptions in relation to a patient, etc.) that are associated in the ontology with the anatomical concepts used in the original query q.

The combo structure KS (that is, the ontology ONTO linked to the geometric model GM) allows overcoming an inherent shortcoming in standalone ontologies which are purely language based. As such there is lack of geometrical or spatial (in particular metric) information in existing ontologies. But thanks to the proposed common processing of the combo-structure, spatial, that is geometric/metrical information, can now not only be queried for, but can also be coded for to accurately represent position, location or other metric information of the concepts coded in the ontology. For instance, the combo structure allows coding location of a stenosis in a vessel based on the geometric model GM being linked to the ontology ONTO. This allows precisely describing and interpreting the location and position of the stenosis or lesion on the vessel or other anatomic component.

Turning now in more detail to the block diagram in FIG. 1, the query q is received at input port IN of the system. The query may be received as a natural language string (not necessarily in controlled vocabulary). Preferably but not necessarily the interface of the system is capable of understanding a natural language query received in any natural language (such as in English, Spanish, German, Chinese, etc), or in a selection of supported languages. The query may be issued by the user in text form. Exemplary embodiments include email, phone text message, or through a search field ("box") in a website configured to interface with input port IN. Alternatively, the query is converted by voice-recognition software interfaced with a signal processing chain to capture the user's voice. Alternatively, the query is used by an application program interfaced with the input port. Specifically, a grabber software, possibly in cooperation with a OCR (optical character recognition) application program, runs on a processing unit to grab the query from a text file, such as a medical report stored in repository maintained in a HIS (hospital information system). The query may be transmitted wirelessly or in a wired communication network to the input IN. The query is understood to relate to one or more anatomies OB of interest and the query relates or includes passages that interrogate for a metric or spatial relationship between the referenced anatomical components as represented in the query.

A suitable parser (not shown) or chunker component parses the query and decomposes same into language string components and one or more relational strings for one or more spatial relations asked for in the query. In this manner, the possibly unstructured query is decomposed into a structured form. The structured form comprises i) strings for the anatomic components ("anatomic strings" or identifiers) of the anatomy OB referred to by the query and ii) the strings for the spatial relation. The anatomic components relate to the whole of the human or animal anatomy or to parts thereof.

The parser however is optional, as there are embodiments envisaged where the query is non-textual, not even voice-based but is for instance specified graphically in an image presented to the user. Using a user-interface arrangement the user specifies a location in visual representation of the anatomy OB of interest displayed on a display unit or in a list view of components for the anatomy. User-interface arrangements envisaged herein include pointer tools (eg, computer mouse) interfaced to suitable event-handler modules. Alternatively, the user-interface arrangement is configured to process specification requests in form of key-board events or touchscreen action, etc. Optionally, based on the specified location, graphical elements are identified at the specified location. The identification operation may be implemented as an image or pattern recognition such as segmentation, in particular as a model-based segmentation. The structured form for such a graphic or location based query is thus formed by a reference to i) the one or more segmented graphical elements and/or ii) to the specified location(s).

The structured form of the query is now mapped by a series of mappers against the ontology linked to the one or more geometric models GM.

More particularly, a concept mapper CM maps the anatomic strings in the decomposed query to one or more (eg, anatomic) concept entries ("linguistic descriptors") in the ontology (ONTO) that are respectively associable with said anatomic strings. As will be explained in more detail below, the ontology ONTO corresponds to a hierarchic (graph structure where these linguistic descriptors are encoded as entries in form of strings or tags. The entries are (logically) connected by edges. The edges represent relations. The edges in the graph structure may be directed or undirected or the graph may include a mix of both, directed edges and undirected edges. The collection of linguistic descriptors of the ontology entries can be understood as a "prototype" of the respective anatomy parts of the object OB. The mapping operation by concept-mapper is essentially an exercise in matching anatomic strings of the decomposed query to the linguistic descriptors (which are likewise strings) in the ontology entries.

A metric mapper MM takes care to map the spatial relations strings extracted from the query by the parser to corresponding metric relationship descriptors. The metric relationship descriptors form an algorithmic representation of the (n-ary, n≥1) spatial relations encoded in the query. Said differently, the metric relationship descriptors form "blue-prints" or schemas for the one or more spatial relationships asked for in the query.

A geometry mapper or geo-mapper GEO fills the language descriptors (mapped onto by the concept mapper CM) with numerical data to enable the system to answer the metrical query. Specifically, the geo-mapper maps the concept entries as per the concept mapper against one or more geometric models GM linked to the ontology. In this manner the linguistic descriptors, as such devoid of metric information, are now loaded with concrete spatial numerical data as per the geometric model. The numerical data includes in particular spatial coordinates relative to a reference frame of the linguistic descriptors of the anatomic components. The link between the linguistic descriptors and the model GM is provided by a set of abstract geometric descriptions as will be explained in more detail below. The geometric model may be a generic one obtained from a cohort of patients or it may be a patient specific one earlier personalized.

A metric component MTC computes the asked for one or more relationships between the mapped onto concepts. Metric components operation is based on the spatial numerical data found by the geo-mapper and the algorithmic description for the one or more metric relationships as found by metric mapper MM. This allows answering in particular metric queries but the coordinates supplied by the geo-mapper and the metric component MTC are also capable of handling a topological query that asks qualitatively for a spatial relationship, eg, such as "Is component A located above component B?". For instance, one set of coordinates along the relevant axis for A and B are compared (eg, subtracted) and the signum of the difference is then used to answer the question.

In some embodiments, the queried relation defines a set of anatomic components that satisfy the asked for relation: For instance, the query may encode asking for all those anatomic components that are within a certain threshold, say 5 cm, of a given anatomic component. In this instance the computation by the metric component implements the algorithm found by the metric mapper MM. As an exemplary embodiment, the mentioned query is implemented by computing differences between positions (as per the numerical data) for the anatomic components and then comparing said differences against the 5 cm threshold to define the set of those linguistic descriptors that satisfy the asked for relation.

The system may comprise a selection component SC that selects said linguistic descriptors which satisfy the asked for spatial relation. The selection component SC then forwards the selection of the identified linguistic descriptors (that represent different anatomy components for the object OB) for further processing, eg for visualization by visualizer VIZ on a display unit MT such as a computer screen. For instance, a visual rendition of the involved geometric model GM may be generated by the visualizer to visually highlight the selected linguistic descriptors for the anatomic components. The visualization may also include displaying annotations for the computed metric relationships. Other visualization options implemented by the visualizer VIZ includes, visually distinguishing by color-coding anatomic components for the non-selected linguistic descriptors from the selected ones as supplied by the selector SC. In this manner, for instance, all anatomic parts that are outside the threshold are rendered in one color (eg, greyed out) whilst all the other anatomic components within the spatial threshold are displayed in a different color. However, the visualization of the involved anatomic concepts is optional. Instead, the answers to the spatial query can be displayed in textual for such as a list without graphical rendering or related anatomic parts of the model GM. The later may be helpful when displaying information on low-resolution hand held computing units in a field setting for instance.

In order to save computing time and/or to prevent information overflow, the system may include a depth level controller DLC. Broadly, the depth level controller DLC restricts operation in particular of the previously mentioned concept mapper components CM. The hierarchy of the ontology ONTO defines different hierarchy levels. For instance, in anatomy context, we have the natural hierarchy of "body→organ→organ structure→sub-organ structure→tissue→cell". For certain computations or queries only a given hierarchy level or all hierarchy levels up to the given level are of interest whilst the remaining lower levels are to be ignored. The depth level controller DLC interfaces with the concept mapper CM and restricts its operation to a range of hierarchy level(s) of interest. In this manner a "granularity level" can be set. The user can pre-set the depth level to which the given query is to extend. Operation of the depth level controller DLC is based on depth level tags which are assigned previously to entries in the ontology. For instance, certain tags identify an entry as an organ whilst other tags relate to cellular components or concepts further down the hierarchy. The depth level controller first identifies all entries that are at the requested depth level to so define a sub-set of ontology entries. The concept mapper is then restricted to only operate on this sub-set of entries and to map the query only to entries in the levels of interest.

Operation of the above mentioned components will now be explained in more detail below.

Referring first in more detail to the ontology ONTO of the combo-knowledge structure KS forms a graph structure with a plurality of entries that represent different linguistic descriptors (strings, but not necessarily in natural language) of autonomic parts or components. These are functionally/logically or otherwise connected by edges of the graph with the entries forming nodes of that graph. Yet more particularly, the ontology is a formal linguistic specification of how to represent relationships among objects, concepts, and other entities belonging to a particular area of human experience or knowledge. In the medical field this refers in particular to the relation of anatomical structures, diseases, medical procedures and findings.

As envisaged herein, entries of the ontology that represent anatomical structures are extended by or linked to respective abstract geometrical descriptions of the anatomical structure referenced by the entry. The abstract geometrical description is implemented in terms of the geometrical model linked to the ontology.

The geometrical 3D model GM linked to the ontology consists in one embodiment of a triangular mesh topology suitable for model-based segmentation. This allows adaptation to medical imagery of a patient. Preferably, labels are assigned to each mesh element. The labels name the anatomical structure the respective mesh element belongs to. The model may be defined at different levels of accuracy/ granularity (multi-scale model). That means the model can cover the whole range of granularity from organs (e.g. heart) and sub-structures (e.g. aortic valve, mitral valve, left coronary artery, . . . ) up to the cellular level and sub-cellular level. Imagery of a patient is obtained, this imagery is segmented and a (generic) mesh model is fitted to the segmented image using the labels. In this manner, personalized models can be built.

Figure 2:
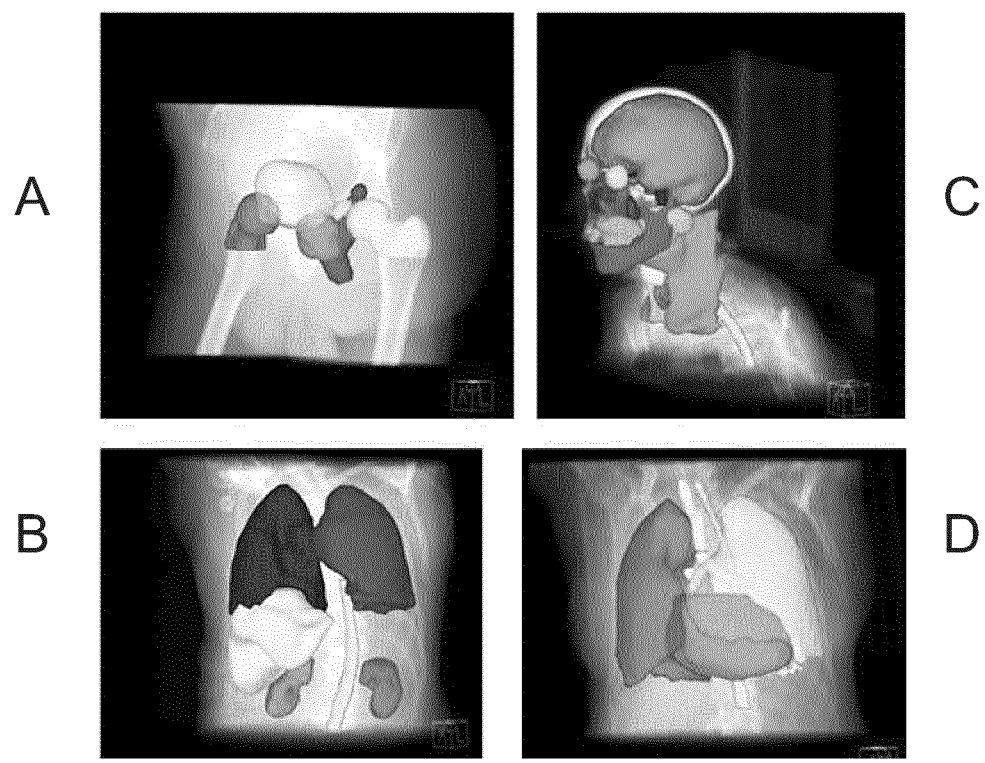
FIG. 2 shows examples of anatomic models.

Examples for geometrical descriptions for different organs are depicted in FIG. 2. Specifically, FIG. 2 shows graphic renderings of four different models as envisaged herein. FIG. 2A shows a model of a male pelvis, FIG. 2B shows an abdominal model, FIG. 2C shows a head and neck model, and FIG. 2D a thorax model.

The linking of the model into the ontology can be done upfront. However, the linking-in may be changed to a different model, if required. Although the model may be hard-coded into the ontology, a soft, or logical linking via referential data structures are preferred in an encapsulated architecture. This makes exchanging of the model for another easier.

It will be understood that the knowledge structure, particularly the ontology may be coded in any suitable format such as XML or other mark-up languages and can be represented in memory in any suitable data structure. The ontology may alternatively be implemented as cross reference tables in the data base system. Yet further, the ontology may be implemented as a set of nested pointer structures. Although the knowledge structure, in particular ontology, can be represented entirely in software hardware, encodings in FPGA's or in hardwired ICs (integrated circuits) are not excluded herein in some embodiments in particular when used in portable devices.

The ontology as proposed herein can comprise static relations (as already known before for ontologies) and novel algorithmic (spatial) relations derived from the query by the metric mapper MM. The novel spatial relations generated by the proposed information retrieval system are new in the sense that they did not exist (that is, were not encoded as entries) in the ontology prior to processing of the received query.

The algorithmic spatial relations AR (shown in FIG. 4 and to be explained in more detail below) as provided by the metric mapper MM are algorithms that are able to evaluate the geometrical description in combination with the linguistic description either when the spatial relation is required (procedural relation) or for the complete ontology at the initial setup (pre-computation of relations). Therefore, a characteristic of the proposed geometry model linked ontology is that it is easily extendable since a new algorithm can be added by the integrator component IC to an already existing set of algorithms. This paradigm is similar to adding an algorithm to a routine library (sometimes referred to as a "toolbox"). Static relations once implemented in the ontology may be kept unchanged alongside the newly included novel algorithmic relations. This is advantageous as not all relations in the ontology are spatial relations (eg, a relation such as "x is a y").

Figure 3:
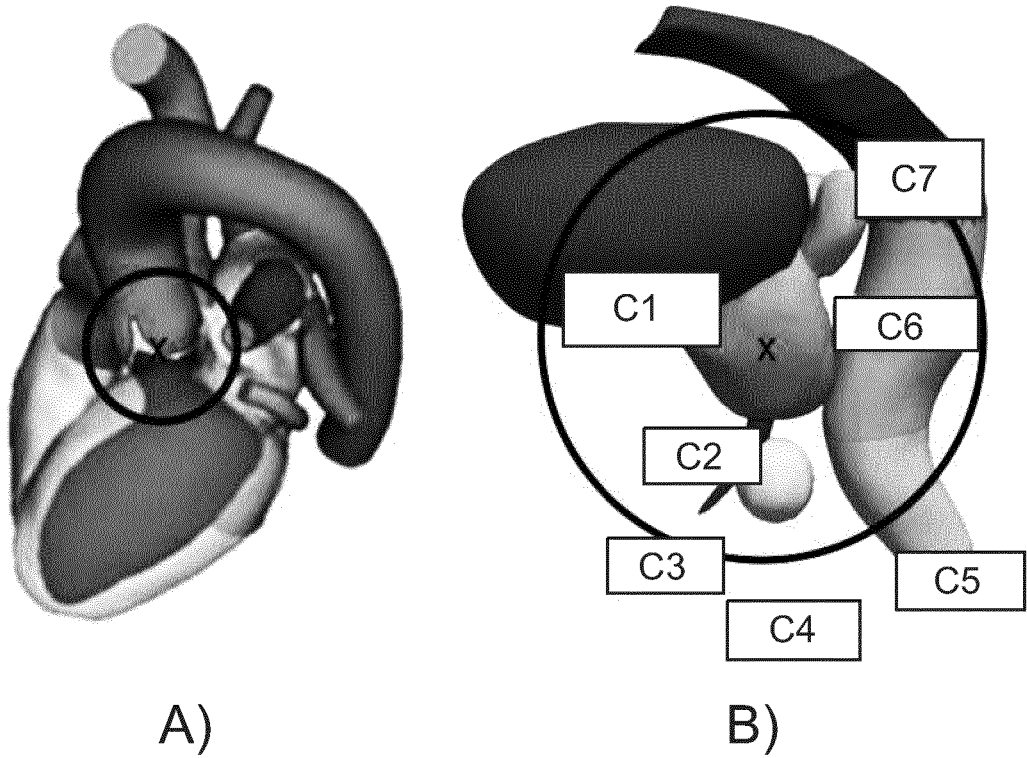
FIG. 3 illustrates computation of spatial relationships based on anatomic models.

Examples of two newly derived spatial relationships are shown in FIG. 3A, B. FIG. 3A shows a geometrical description of a heart. For the ontology entry/linguistic description "aortic valve" the algorithmic spatial relation "in the neighborhood" is evaluated by metric mapper MTC. So the algorithm starts the search in the middle of the geometrical description of the ontology entry/anatomical structure. In the example at hand this is the middle of the aortic valve (marked with a cross in the image which corresponds to a point in the geometric description). For each ontology entry/anatomical structure, its granularity or hierarchical level is given. Granularity level depends on the size of the anatomy and its hierarchical level in the anatomy (e.g. body→organ→organ structure→sub-organ structure→tissue→cell). Depending on the granularity level, the search range in the geometrical description is defined by depth level controller DPL (by convention, the level is the lower the smaller the referenced anatomical structure. An abstract geometrical description is evaluated by metric component MTC within the defined hierarchic level(s). Said differently, the metric component runs a search to find all those linguistic descriptors (end hence their associated geometrical descriptions) that satisfy the asked for relation. Specifically, in case of a geometrical description in terms of mesh elements (eg, triangles in case of a triangular mesh, or elements of other shape in non-triangular meshes), for each geometrical description it is looked up by the metric component MTC whether the mesh elements is within the specified search range (eg, 5 cm neighborhood) as per the query. Since all geometrical descriptions so found are linked to an ontology entry, it is ensured that all relevant linguistic descriptors of the anatomical structure within the search range have likewise been found. If the linguistic descriptors found are on the same granularity/hierarchical level, the names of the anatomical structures/linguistic descriptors/ontology entries are optionally displayed by the visualizer VIZ on the display device MT.

Another example is depicted in FIG. 3B. The labels in FIG. 3B include anatomic components $C_j$ of a model. Specifically, C1 for bladder, C2 for the prostate, C3 for the urethra, C4 for the penile bulb, C5 for the anal canal, C6 the seminal vessel and C7 for the rectum. The anatomic components C1-C7 make up the part of the anatomy OB as per the model in FIG. 3B. FIG. 3B represents the result of an evaluation of the spatial relation "in the neighborhood of" relative to the prostate. The models, patient specific or generic, can be thought to represent a prototype of the respective anatomy.

Figure 4:
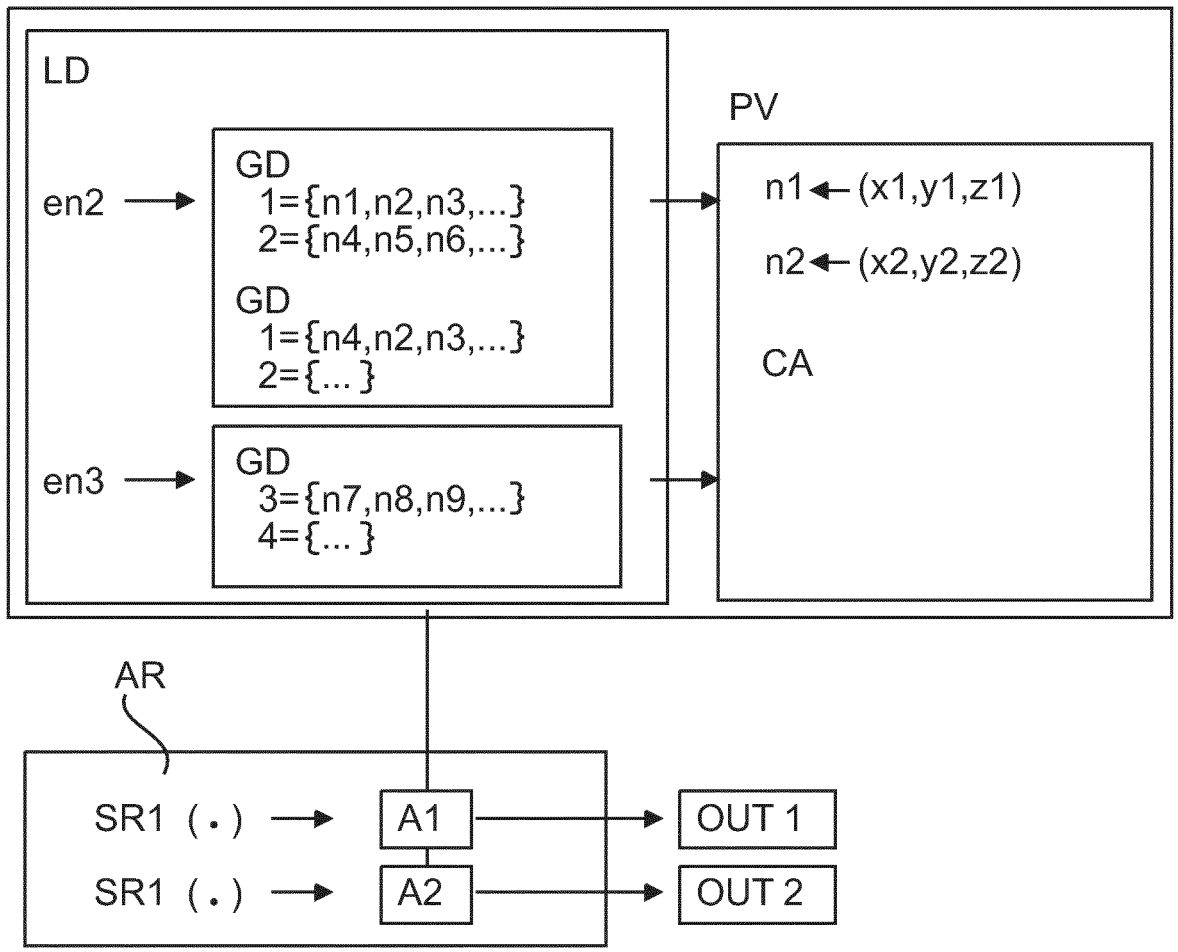
FIG. 4 shows part of a knowledge structure as employed in the system of FIG. 1.

Referring now to FIG. 4, this shows schematically a part of the knowledge structure KS, in particular the ontology ONTO linked to the geometrical model GM as envisaged herein. The ontology ONTO comprises a plurality of interlinked entries en2, en3, etc, each entry representing a respective linguistic description of anatomic parts/components of the anatomy OB. Each linguistic description entry en2, en3 is associated with a respective abstract geometric description GD of the respective anatomy part. This abstract geometric description describes a topology in co-ordinate free form of the anatomic part/component represented by the respective entry en2,en3. The abstract geometric description comprises in one embodiment a listing of the respective geometric (eg, mesh) elements $\Delta 1$, $\Delta 2$, of the model GM. This constitutes the link between the ontology and the geometrical model as indicted by the first set of arrows to the left in FIG. 4. Each of the mesh elements is made up of respective nodes $n_j$.

In one embodiment ontology is configured to encode anatomic variances of a given anatomic component. In other words, rather than having merely one abstract geometric description CA for a given anatomy part, there are one or more alternative descriptions CB. The anatomic variances may be described by different mesh elements. As an example for anatomical variants, the conus branch of the coronary tree can derive from the aorta (anomaly, 20-30% of all cases) or from the right coronary artery (RCA, normal case). Also in 40% the sinus node artery originates from the LCX (anomaly) instead of the RCA (normal case). For the physician or the application it might be relevant that the relations of the ontology describe the correct physiology of the patient.

The linkage between the linguistic descriptor entries en1, en2 with their respective abstract geometric description of a generic or patient specific model represents the "marriage" between language concepts and geometry as envisaged herein. The linked in abstract geometric descriptions may suffice to derive qualitative spatial relations. Indeed for some queries envisaged herein this maybe enough. As a refinement of this, in the preferred embodiment, the proposed information retrieval system is capable of answering quantitative queries. In order to ensure quantitative query processing, the geometric model (linked to the ontology) is loaded with numeric data PV, such as patient data derived from segmented medical imagery. This data may also represent average locations obtained from imager of a cohort of patients. This second linkage is shown as the second set of arrow to the right of FIG. 4. The numeric data $(x_i, y_i, z_i)$ represents in particular co-ordinates (relative to a given co-ordinate frame) of the nodes $n_j$ of mesh elements $\Delta_j$ of a patient specific (personalized) or generic model (as derived by taking the averages of a plurality of personalized models). Specifically, co-ordinates $x_i, y_i, z_i$ are assigned to the respective nodes $n_j$ that make up the respective mesh elements $\Delta j$. The abstract geometric description GD of the variants CB, CA is equally loaded with numerical data. The metric relationship descriptors AR as extracted by the geomapper GEO can be thought of as different spatial algorithmic relations SR1, SR2 that are configured to operate on the above numerical data PV to produce respective outputs OUT1, OUT2, that is, answers to the query q. An integrator component IC may optionally link the newly formed algorithm relations SR1, SR2 into the ontology ONTO, in association with the respective linguistic descriptor LD entry that represents the anatomic components referenced in the query q. It will be appreciated that in this sense the result of the queries can be encoded at persistent data into the knowledge structure KS in particular it can be associated to entries of the ontology. In this manner, the newly derived relations AR can be linked added to the ontology like algorithms to a toolbox.

It will be appreciated that the concrete numerical data (the coordinates $(x_i, y_i, z_i)$) PV is decoupled from the ontology and preferably only softly linked to the abstract geometrical description GD. E.g., the numerical data (that is, the concrete values for the abstract geometrical description) may be stored in a separate file. The file with the patient values PV is therefore easily exchangeable and not part of the ontology itself. If the abstract geometrical description is, for example, a mesh topology, the patient-specific file contains the coordinates of the mesh nodes as illustrated in FIG. 4. If no patient-specific values are available for the patient or only for a part of the anatomical structures, a file with mean values for a patient cohort can be loaded instead and linked into the ontology. The numerical data in PV may be grouped according to anatomical variants (if any) to be able to the correct numerical data.

Preferably, a qualitative algorithmic relation AR may be called with a parameter by the metric component MTC. This parameterized calling allows answering quantitative queries. For instance, rather than a qualitative query "in the neighborhood of", we can call the query with a parameter x such as "in neighborhood of x cm". Calling the algorithm AR with a parameter defines a specific constraint with which the algorithm AR evaluates the geometrical description and a quantitative result is obtained. Note that quantitative spatial relations make more sense for patient-specific ontologies than for those that refer to an average patient cohort (although an evaluation is possible in both cases).

In one embodiment the geometrical description GD linked to the ontology ONTO is a probabilistic geometrical model (e.g. a probabilistic atlas). Hence, an evaluation of an algorithmic spatial relation AR with a probabilistic result is possible. An example for a probabilistic relation is "anomaly" of a specific organ "with a probability of % percent".

The proposed system IPS as explained herein may be implemented as a software suite on a general computing or processing system PU, for instance, in a hospital information system (HIS) or similar. The information retrieval system may be arranged in a central unit, such as a server, to receive queries from a number of different users, possibly located at different hospital facilities or sites. The proposed system IPS may be arranged in a distributed architecture connected in a suitable communication network. For instance, one or more (or all) of the mappers CM,MM,GEO may be arranged at the user-interface arrangement. The mapping signals are transmitted to the ontology which may be stored remote from the user/user-input arrangement. The metric component MTC may likewise reside at the user or in a server. The above is an exemplary embodiment of a distributed architecture but any other combination of distributions of the information retrieval system components across the network are also envisaged herein in alternative embodiments.

In a further embodiment the information retrieval system can also be stored as executables on a hand held device such as a smart phone, laptop, tablet or otherwise.

Figure 5:
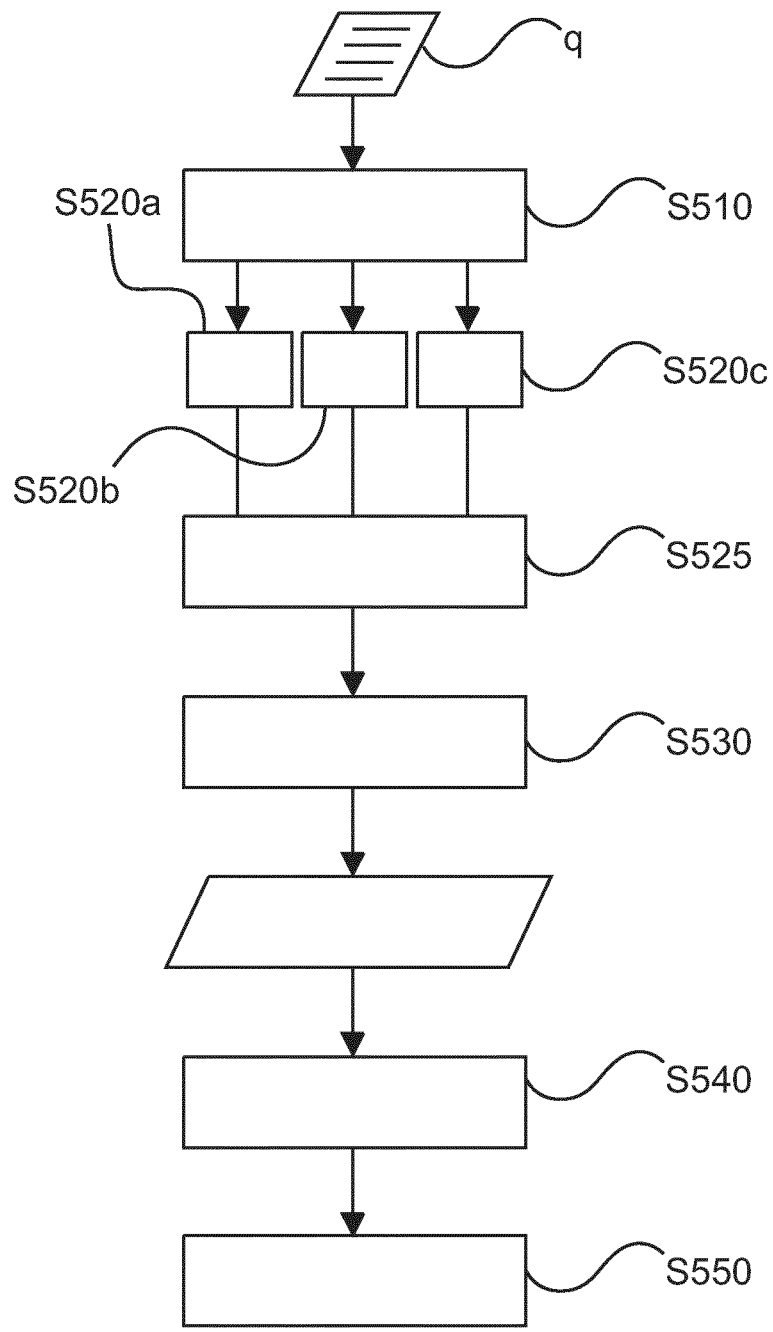
FIG. 5 shows a flow chart of a method of retrieving information.

Lastly the proposed information retrieval system and/or the method as per FIG. 5 may be implemented in hardware as in an FPGA (field programmable gate array) or as a hardwired integrated circuit (IC).

Reference is now made to FIG. 5 which summarizes the underlying operation of the proposed information retrieval system as per FIG. 1. However, it will be understood that the following method steps constitute a teaching in their own right and are not necessarily tied to the architecture of the information retrieval system as shown in FIG. 1.

At step S510 a query in relation to an object of interest such as a part of a human or animal anatomy is received. The "object of interest" should be understood broadly and may also relate to the whole of the human or animal anatomy.

At step S520a the query is mapped to one or more concept entries of a hierarchic graph structure such as an ontology. The entries in this data structure encode respectively linguistic descriptors of anatomic components of a prototype or model GM of the object of interest OB.

At step S520b the query is mapped to one or more metric relationship descriptors. The metric relationship descriptors represent one or more metric or spatial relations that are asked for in the received query.

At step S520c the mapped onto concept entries of step S520a are mapped onto a geometric model to obtain spatial numeric data which is associated with the linguistic descriptor via a model linked to the hierarchic graph data structure. The numeric data includes in particular co-ordinates (relative to a given common reference co-ordinate frame) of mesh elements in the model GM.

Optionally, there is a step S525 where the mapping operation of concept mapper S520a is restricted to concept entries at or up to a pre-defined hierarchic level in the hierarchic graph data structure.

At step S530 one or more metric relationships are computed between the object components, based on the spatio-numerical data (in particular, the coordinates) derived from step S520c and the one or more metric relationship descriptors as mapped onto in step S520b.

Optionally, at step S540, all those linguistic descriptors from the ontology are selected that satisfy the one or more spatial relationships as per the metric relationship descriptors.

At optional step S550 a visualization of the prototype is rendered on a display device based on the model. The visualization so generated includes in particular graphical mark-ups of the model components represented by the selected linguistic descriptors.

The proposed system and method allow a user to quickly consolidate potentially vast amounts of information that is otherwise difficult to query. The implementation of the proposed system and method is based on the combo-structure formed by ontology, but includes abstract and concrete geometric information whose processing together has been observed to yield substantial computational efficiencies. This can lead to very quick turn arounds which is especially beneficial in busy clinical environments where a central computer is usually used to serve queries from large numbers of hospitals across a region such as in big city or urban conglomerates.

In sum, the proposed system and method allows securing efficient usage of expensive computational infrastructure which is a distinct advantage in the ever busy environments of national health services. The proposed system and method allow harnessing language based concepts knowledge in ontologies and to put these to use in context where spatial information are or interest.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An information retrieval system configured to compute one or more metric or spatial relationships, comprising:
an input interface for receiving a query related to an atomical object of interest, wherein the query includes a spatial relation string with a question regarding a spatial relation between the anatomical object of interest and another anatomical object and a metric relation string with a request for a numerical geometric value of a spatial relation between the anatomical object of interest and the anatomical object;
a concept mapper configured to map anatomic strings in the query to one or more associated concept entries of a hierarchic graph data structure ontology, wherein the entries in said structure encode linguistic descriptors of components of a model for said object, and the linguistic descriptors do not include spatio-numerical data;
a metric-mapper configured to map the one or more spatial relation strings in the query to one or more metric relationship descriptors, wherein the one or more metric relationship descriptors form an algorithmic representation of the one or more spatial relations;
a geo-mapper configured to map said concept entries against a geometric model linked to the hierarchic graph data structure to obtain spatio-numerical data associated with said linguistic descriptors; and a metric component configured to compute one or more metric or spatial relationships between said anatomical object of interest and one or more objects based on the spatio-numerical data and the one or more metric relationship descriptors, wherein the computed one or more metric or spatial relationships answers the query.

2. The information retrieval system of claim 1, comprising a selection component configured to select from the one or more objects satisfying the one or more metric relationships.

3. The information retrieval system of claim 2, comprising an output interface for outputting a representation of the linguistic descriptors of the selected components.

4. The information retrieval system of claim 1, comprising a visualizer, configured to render, based on the model, a visualization of the geometric model or a related model on a displaying device, said visualization including a representation of the selected components.

5. The information retrieval system of claim 1, comprising a depth-level controller configured to restrict the mapping operation of the concept mapper to concept entries at or up to a pre-defined depth level in the hierarchic graph data structure.

6. The information retrieval system of claim 1, wherein the geometric model is a probabilistic geometric model.

7. The information retrieval system of claim 1, wherein the object is an anatomy of a human or animal patient, and wherein the model is a generic model or a specific patient model.

8. The information retrieval system of claim 1, comprising an integrator component configured to integrate i) the computed relationships or ii) the one or more metric relationship descriptors into the hierarchic graph data structure.

9. The information retrieval system of claim 1, wherein the numeric data includes coordinates relative to a given common reference coordinate frame of mesh elements in the model.

10. The information retrieval system of claim 9, wherein the metric component is configured to compute a relationship of the one or more metric or spatial relationships based on a signum of a difference between the anatomical object of interest and the other anatomical object based on the coordinates along an axis for the anatomical object of interest and the other anatomical object.

11. The information retrieval system of claim 1, wherein the query asks for all components of the anatomical object of interest that are within a predetermined distance of the other anatomical object.

12. The information retrieval system of claim 1, wherein the algorithmic representations evaluate a geometrical description in combination with a linguistic description either when a spatial relation is required or for a complete ontology at an initial setup.

13. The information retrieval system of claim 1, wherein the computed one or more metric or spatial relationships were not previously encoded in the ontology before the computation of the computed one or more metric or spatial relationships, and the metric component is further configured to add the computed one or more metric or spatial relationships to the ontology.

14. An information retrieval method for computing one or more metric or spatial relationships, comprising:

receiving a query related to an object of interest, wherein the query includes a spatial relation string with a question regarding a spatial relation between the object of interest and another object and a metric relation string with a request for a numerical geometric value of a spatial relation between the object of interest and the other object;

mapping anatomic strings in the query to one or more associated concept entries of a hierarchic graph data structure, the entries in said structure encoding linguistic descriptors of components of a model for said object, wherein the linguistic descriptors do not include spatio-numerical data;

mapping the one or more spatial relation strings in the query to one or more metric relationship descriptors, wherein the one or more metric relationship descriptors form an algorithmic representation of the one or more spatial relations;

mapping said concept entries against a geometric model linked to the hierarchic graph data structure to obtain spatio-numerical data associated with said linguistic descriptors; and computing one or more metric or spatial relationships between said anatomical object of interest and one or more objects based on the spatio-numerical data and the one or more metric relationship descriptors, wherein the computed one or more metric or spatial relationships answers the query.

15. The method of claim 14, comprising selecting from the one or more objects satisfying the one or more metric relationships.

16. The method of claim 14, comprising rendering, based on the geometric model, a visualization of the prototype on a displaying device, said visualization including a representation of the selected components.

17. The method of claim 14, comprising restricting the mapping operation of the concept mapper to concept entries at or up to a pre-defined depth level in the hierarchic graph data structure.

18. The method of claim 14, wherein the hierarchic graph data structure includes an ontology.

19. A non-transitory computer program element, which, when being executed by a processing unit is adapted to perform the method of claim 14.

20. A non-transitory computer readable medium encoded with a computer readable instruction, which, when executed by a processor, causes the processor to:

receive a query related to an object of interest, wherein the query includes a spatial relation string with a question regarding a spatial relation between the object of interest and another object and a metric relation string with a request for a numerical geometric value of a spatial relation between the object of interest and the other object;

map anatomic strings in the query to one or more associated concept entries of a hierarchic graph data structure, the entries in said structure encoding linguistic descriptors of components of a model for said object, wherein the linguistic descriptors do not include spatio-numerical data;

map the one or more spatial relation strings in the query to one or more metric relationship descriptors, wherein the one or more metric relationship descriptors form an algorithmic representation of the one or more spatial relations;

map said concept entries against a geometric model linked to the hierarchic graph data structure to obtain spatio-numerical data associated with said linguistic descriptors; and compute one or more metric or spatial relationships between said anatomical object of interest and one or more objects based on the spatio-numerical data and the one or more metric relationship descriptors, wherein the computed one or more metric or spatial relationships answers the query.

\* \* \* \* \*